United States Patent [19]

Leung et al.

[11] Patent Number: 4,849,329
[45] Date of Patent: Jul. 18, 1989

[54] PROCESS FOR PREPARING LYMPHOKINE ACTIVATED KILLER CELLS

[75] Inventors: Kam H. Leung, Brookhaven, Pa.; John J. Rinehart, Columbus, Ohio

[73] Assignee: E. I. Du Pont de Nemours and Company, Wilmington, Del.

[21] Appl. No.: 38,361

[22] Filed: Apr. 20, 1987

Related U.S. Application Data

[63] Continuation-in-part of Ser. No. 868,697, May 30, 1986, abandoned.

[51] Int. Cl.$^4$ .............................................. A01N 1/02
[52] U.S. Cl. .......................................... 435/2; 424/93; 424/101; 514/2; 514/21; 604/4; 435/240; 435/241
[58] Field of Search ..................... 424/101, 93; 514/2; 435/2, 240, 241; 604/4

[56] References Cited

U.S. PATENT DOCUMENTS 4,752,602  6/1988  Lipsky et al. ........................ 514/19

OTHER PUBLICATIONS

Thiele, et al., *Journal of Immunology*, 134, 786–793 (1985).
Lanier, et al., *Journal of Immunology*, 134, 794–801 (1985).
Rayner, et al., *Cancer*, 55, 1327–1333 (1985).
Shau, et al., *Journal of Immunology*, 134, 1136–1141 (1985).
Thiele, et al., *Journal of Immunology*, 131, 2282–2290 (1983).
Thiele, et al., *Proc. Natl. Acad. Sci. USA*, 82, 2468–2472 (1985).
Mangan, et al., *Infection and Immunity*, 46, 332–339 (1984).
Meineke, et al., *Fed. Proc.*, 44, 1688 (1985).
Rosenberg, et al., *The New England Journal of Medicine*, 313, 1485–1492 (1985).
Hoyer, et al., Cancer Research 46, 2834–2838 (1986).
Leung, Lymphokine Research 6, 1718 (1987).

*Primary Examiner*—Matthew A. Thexton
*Assistant Examiner*—Catherine S. Kilby

[57] ABSTRACT

There are disclosed an improved process for preparing lymphokine activated killer (LAK) cells from peripheral blood mononuclear cells, a composition consisting essentially of the LAK cells prepared from the disclosed process in a pharmaceutically acceptable carrier, and a method of treating cancer comprising administering the disclosed composition to a patient suffering from said cancer.

37 Claims, No Drawings

PROCESS FOR PREPARING LYMPHOKINE ACTIVATED KILLER CELLS

CROSS-REFERENCE TO RELATED APPLICATION

This is a continuation-in-part of copending patent application Ser. No. 868,697, filed on May 30, 1986 now abandoned.

BACKGROUND OF THE INVENTION

1. Field of the Invention

This invention relates to a process for preparing lymphokine activated killer (LAK) cells and to a method of adoptive transfer therapy using the cells so prepared.

2. References

Thiele, et al., *Journal of Immunology* 134, 786–793 (1985), disclose that L-leucine methyl ester (Leu-OMe) causes lysosomal disruption and death of human monocytes. In addition, L-leucine methyl ester removed natural killer cell (NK) activity from human peripheral mononuclear cells. The authors disclose that a brief preincubation of human peripheral mononuclear cells with Leu-OMe (1 to 5 mM) caused irreversible loss of NK function as assessed by lysis of K562 target cells. They report that a variety of other amino acid methyl esters, including L-glutamic dimethyl ester, L-valine methyl ester, and L-isoleucine methyl ester caused reversible inhibition of NK activity but did not cause irreversible loss of all NK function. Even when much higher concentrations of the other various amino acid methyl esters were used, only L-glutamic dimethyl ester was found to be able to effect NK function irreversibly. Only Leu-OMe and L-glutamic dimethyl ester were found to be toxic towards human monocytes. The authors do not mention phenylalanine methyl ester.

Lanier, et al., *Journal of Immunology* 134, 794–801 (1985), disclose that highly purified recombinant interleukin-2 markedly augments the natural killer cell-mediated cytotoxicity of peripheral blood lymphocytes. The authors report that all recombinant interleukin-2 responsive cytotoxic NK cells were found within the subset of lymphocytes expressing the Leu 11 marker, an antigen associated with the Fc-IgG receptor on human NK cells. Activation of Leu 11+NK cells resulted from a direct effect of recombinant interleukin 2 on these cells and neither required nor was amplified by the presence of T lymphocytes.

Rayner, et al. *Cancer* 55, 1327–1333 (1985), disclose that lymphokine-activated killer (LAK) cells can be generated by incubating fresh peripheral blood lymphocytes in interleukin-2. The authors disclose that LAK cells kill fresh autologous and allogeneic human tumor cells in vitro. The LAK cells can be generated from preipheral blood lymphocytes of normal individuals and tumor-bearing patients. They report that pure, recombinant interleukin-2 generates LAK cells capable of killing a wide variety of tumors including sarcomas and cancers of the colon, pancrease, adrenal gland, and esophagus. The authors state that the LAK system is distinct from the natural and classic cytolytic T-lymphoid systems. LAK cells, generated in recombinant interleukin-2, can lyse NK-resistant tumor cells. They report that the use of LAK cells, possibly with the systemic administration of rIL-2, represents a promising future approach to the immunotherapy of human cancer.

Shau, et al., *Journal of Immunology* 134, 1136–1141 (1985), disclose that human natural killer cell activity in peripheral blood lymphocytes is totally inhibited by pretreatment of the effector cells with a lysosomotropic agent, L-leucine methyl ester. The authors further report that natural killer activity can be regenerated in the NK cell-depleted peripheral blood lymphocyte population by incubation with IL-2 or by mixed lymphocyte cultures.

Thiele, et al., *Journal of Immunology* 131, 2282–2290 (1983), disclose the use of the lysosomotropic compound L-leucine methyl ester to delineate the phenotype of the accessory cells involved in human B and T cell activation in vitro. They report that L-leucine methyl ester (Leu-OMe) caused lysosomal disruption and selective death of human monocytes and that Leu-OMe preincubation abolishes mitogen-induced lymphocyte responses. Responsiveness was completely restored by coculture with a monocyte enriched glass adherent cell population.

Thiele, et al., *Proc. Natl. Acad. Sci. USA* 82, 2468–2472 (1985), disclose that when mononuclear phagocytes or polymorphonuclear leukocytes were incubated with Leu-OMe, there is formed L-leucyl-L-leucine methyl ester (Leu-Leu-OMe), which elimianted all NK function from mixed lymphocyte populations. They report that this effect did not require the presence of mononuclear phagocytes or polymorphonuclear leukocytes. When amino acids with nonpolar R groups were substituted for leucine in either position, the resulting dipeptide methyl ester was generally found to display at least some degree of NK toxicity. The authors further reported that previous experiments had shown that compounds such as valine methyl ester and phenylalanine methyl ester or combinations thereof did not delete NK function from human peripheral blood mononuclear cells.

Mangan, et al., *Infection and Immunity* 46, 332–339 (1984), disclose that removal of monocytes from unfractionated cells by several means, including the use of Leu-OMe, resulted in a population of cells responsive to *Fusobacterium nucleatum* induced polyclonal B-lymphocyte activation (PBA) and unresponsive to PBA induced by pokeweed mitogen.

Meineke, et al., *Fed Proc* 44, 1688 (1985), disclose that when peripheral blood mononuclear cells were depleted to 4% monocytes by adherence to plastic, or nylon wool or by treatment with L-leucine methyl ester, enhanced LAK activation and reduced cell concentration dependency was seen after removal of the monocytes by each technique.

Rosenberg, et al., *The New England Journal of Medicine* 313, 1485–1492 (1985), disclose preliminary results of the systemic administration of autologous lymphokine-activated killer cells and recombinant IL-2 to patients with advanced cancer. They treated 25 patients with metastatic cancer in whom standard therapy had failed. Objective regression of cancer (more than 50 percent of volume) was observed in 11 of the 25 patients. Complete tumor regression occurred in one patient with metastatic melanoma and had been sustained for up to 10 months after therapy.

In the effort to further investigate and refined LAK cells and rIL-2 as an adoptive immmunotherapy for cancer, improvements which enhance the activity of the LAK cells, or which allow activation at a higher concentration of cells or otherwise offer increased attractiveness of the therapy are most desirable.

SUMMARY OF THE INVENTION

The present invention provides an improved process for preparing lymphokine activated killer (LAK) cells. In the process wherein peripheral blood mononuclear cells are cultured to produce a population of cells which are cytotoxic for fresh tumor cells, the improvement comprises contacting the peripheral blood mononuclear cells or peripheral blood lymphocytes resulting therefrom, prior to culturing said cells, with an L-amino acid lower alkyl ester or hydrogen chloride salt thereof wherein the L-amino acid is selected from the group consisting of alanine, aspartic acid, cysteine, glutamic acid, glutamine, phenylalanine, proline, tyrosine, tryptophan and valine or a mixture of any of the foregoing, and thereafter culturing the resulting cells. The invention also provides an improved composition consisting essentially of isolated LAK cells prepared pursuant to the foregoing process, said cells being dispersed in a pharmaceutically acceptable carrier and being reactive to tumor when administered with interleukin-2 to a human afflicted with said tumor. Also, included within the present invention is a method for treating cancer in humans comprising administering to a human suffering from said cancer interleukin-2 and a tumor size-reducing effective amount of the foregong composition.

DETAILED DESCRIPTION OF THE INVENTION

As used herein:

"Interleukin-2" (IL-2) means human interleukin-2 which is a glycoprotein with a molecular weight of approximately 15,000 daltons and consists of a 133 amino acid polypeptide containing a single disulfide bridge. The term, as used herein, includes natural and recombinant interleukin-2 (rIL-2) and biologically functional equivalents thereof. "Biologically functional equivalents" mean polypeptides having the same or very similar biological activity, such as the rIL-2 muteins described in U.S. Pat. No. 4,518,584 and rIL-2 proteins having a methionine replacing the $NH_2$-terminal alanine found in native IL-2. The disclosure of U.S. Pat. No. 4,518,584 in regard to rIL-2 muteins is incorporated herein by reference. These muteins are rIL-2 molecules wherein the cysteine at position 125, numbered in accordance with native human IL-2, is deleted or replaced by a neutral amino acid and said mutein exhibits the biological activity of native human IL-2.

"Lymphokine activated killer (LAK) cells" means a cytotoxic population of cells which are capable of lysing autologous tumor cells and NK-cell resistant tumor cell lines and are generally prepared by culturing peripheral blood mononuclear cells with interleukin-2.

"Consisting essentially of" means that the particular composition(s) with which the phrase is used can contain other ingredients so long as they do not materially alter the basic and novel characteristics of the composition, e.g., its high LAK activity at high cell concentration.

"Peripheral blood lymphocytes" means peripheral blood mononuclear cells from which monocytes have been depleted.

"Lower alkyl" means alkyl group of 1–4 carbon atoms.

It has been found that LAK-cell induction is inhibited at high cell concentrations, e.g. $2.5 \times 10^6$ cells/mL. The process of the invention enables LAK-cell induction at 5–10 fold higher cell concentrations without altering the extent or range of LAK-cell activity. Although the invention will be described in specific with reference to human peripheral blood mononuclear cells or human peripheral blood lymphocytes, it is to be understood that the invention applies to the corresponding cells of other mammals. Preferably, the invention is used with human cells and for treatment of humans.

In the process of the invention, LAK cells are prepared by contacting human peripheral blood mononuclear cells (PBMC) or peripheral blood lymphocytes with a specified amino acid lower alkyl ester or hydrogen chloride salt thereof. Contacting is carried out for a period of at least about 15 minutes, preferably from about 20 minutes to about 40 minutes. The resulting cells are then cultured to produce a population of cytotoxic cells which will lyse fresh tumor cells.

In the process of the invention PBMC can be obtained by Ficoll-Hypaque density gradient separation of ethylenediaminetetraacetic acid (EDTA)-anticoagulated venous blood drawn from healthy donors. The cells are then washed with a suitable salt solution, such as Seligman's balanced salt solution (SBSS), which is obtainable fron Gibco, Grand Island, N.Y.), and then resuspended in a suitable medium, such as RPMI 1640 medium, which is obtainable from M.A. Bioproducts, Walkerville, Md., supplemented with 1 mM L-glutamine solution, 1% penicillin-streptomycin solution, 1% antibiotic-antimycotic solution, 20 mM HEPES (Gibco, Grand Island, N.Y.) and 10% heat inactivated pool human serum (HIS) (percentages are v/v unless otherwise specified). Other suitable media are well known, see, for example, Rosenberg, et al., The New England Journal of Medicine 313, 1485, 1486 (1985).

The resuspended PBMC are then contacted with the L-amino acid lower alkyl ester or hydrogen chloride salt thereof. L-Amino acid lower alykl esters suitable for use in the process of the invention are those wherein the amino acid is selected from the group consisting of alanine, aspartic acid, cysteine, glutamic acid, glutamine, phenylalanine, proline, tyrosine, tryptophan and valine or a mixture of any of the foregoing. Preferably, the L-amino acid is phenylalanine or tyrosine and most preferably is phenylalanine. The lower alkyl group can be methyl, ethyl, propyl, isopropyl, butyl, isobutyl or t-butyl but is preferably methyl or ethyl and is most preferably methyl. The PBMC can be resuspended in any suitable medium such as serumless RPMI 1640. Preferably, the hydrogen chloride salt of the L-amino acid lower alkyl ester is dissolved in RPMI and the pH of the resulting solution is adjusted to about 7.4 prior to adding the resulting solution to the suspension of PBMC. The amino acid lower alkyl ester is present at a concentration of from about 1 mM to about 5 mM (based on the total volume of the combined PMBC suspension and the amino acid lower alkyl ester solution). Contacting is preferably carried out at a temperature of from about 20° C. to about 25° C.

In another embodiment of the invention, monocytes are depleted from the PBMC prior to treatment with the amino acid lower alkyl ester. Depletion can be effected with conventional techniques such as use of iron carbonyl or passage of the PBMC over glass beads. Then the resulting peripheral blood lymphocytes are treated with the amino acid lower alkyl ester as set forth above.

In the process of the invention, when the PMBC are contacted with the L-amino acid lower alkyl ester prior to depletion of monocytes, the treatment with L-amino acid lower alkyl ester causes depletion of monocytes and also confers on the ultimate LAK cell product enhanced activity at higher cell concentration. When depletion of monocytes is effected prior to treatment with the ester, the treatment still confers the enhanced activity. In the preferred embodiment of the invention the PBMC are contacted with the L-amino acid lower alkyl ester without prior depletion of the monocytes. It is to be understood that for purposes of the present invention, monocytes are considered to be depleted when the number percent of monocytes present based on the total number of PBMC present is less than about 10%.

In another embodiment of the invention, the PMBC can be contacted with the amino acid lower alkyl ester prior to Ficoll-Hypaque density gradient separation. Thereafter, density gradient separation and the other steps of the process of the invention are carried out. The resulting monocyte-depleted PBMC are then washed with a suitable solution, such as SBSS, and resuspended in cRPMI—105 HIS or other suitable medium.

The suspension of monocyte-depleted PBMC (peripheral blood lymphocytes) is next cultured for an incubation period of from about 2 to 7 days, preferably, at about 35° C. to 39° C., most preferably 37° C. Preferably, culturing is effected in the presence of from about 3%–7% by volume $CO_2$, most preferably 4% $CO_2$. Preferably, the peripheral blood lymphocytes are suspended at a cell concentration of from about $2 \times 10^5$ to about $2 \times 10^7$, most preferably from about $5 \times 10^6$ to about $1 \times 10^7$. Culturing can be done in a suitable medium in the absence of IL-2; however, preferably, culturing is performed in the presence of IL-2. When peripheral blood mononuclear cells or peripheral blood lymphocytes are treated with an L-amino acid lower alkyl ester according to the present invention, culturing in the presence of IL-2 can lead to about a four-fold to five-fold increase in LAK activity as compared to culturing in the absence of IL-2. Increased LAK activity is exhibited against NK-cell resistant tumor cells and NK-cell sensitive tumor cells. Preferably, the IL-2 concentration is from about $1.5 \times 10^2$ to about $1.5 \times 10^4$ pM, most preferably from 1000 pM to about 2000 pM. Preferably, the IL-2 used is rIL-2, and, most preferably, the rIL-2 is a rIL-2 composition consisting essentially of water, rIL-2, and optionally, a polyol, said composition having an IL-2 specific activity of at least about 120,000 units/mg, said specific activity being at least 40% of that of Jurkat IL-2. This rIL-2 composition is described in U.S. patent application Ser. No. 825,133, filed on Jan. 31, 1986 and assigned to E. I. du Pont de Nemours and Company, which is incorporated herein by reference. This rIL-2 composition is prepared by a process comprising (a) mixing with water to generate a suspension rIL-2 which has been lyophilized after purification by high performance liquid chromatography, and (b) heating the resulting suspension at a temperature of from about 25° C. to about 95° C. for at least about two hours. Culturing can be performed in conventional containers, such as T-flasks, petri dishes, cluster dishes and polypropylene tubes.

LAK cells prepared pursuant to the process of the invention, result in higher activity than untreated cells and a high yield of lytic units. The LAK cells can be suspended in a pharmaceutically acceptable carrier, such as saline, saline containing 5% normal human serum albumin, or Hanks' balanced salt solution, to provide a composition which can be infused into a patient afflicted with a tumor. The patient is concurrently treated with rIL-2 as further described by Rosenberg, et al., The New England Journal of Medicine 313, 1485–1492 (1985). In that modality, the patients blood is withdrawn, subjected to leukapheresis and harvested cells are immediately cultured to generate LAK cells. The LAK cells are infused into the patient within about three days. Typically, about $3 \times 10^{10}$ to $14 \times 10^{10}$ LAK cells are infused in 4–9 doses. Interleukin-2 is administered every eight hours at a dose such as 10,000, 30,000, or 100,000 units per kilogram of weight. The treatment consists of a two-week treatment of leukapheresis and reinfusion and generally repetition starting the third week. Recombinant IL-2 can be included in the LAK cell composition.

The present invention can be carried out by the herein-described specific embodiments but is not limited thereto. The invention is further illustrated by the following examples in which all percentages are by volume and temperatures are in degrees Celsius, unless otherwise stated.

Cytotoxicity Assay

Unless otherwise stated, a 4 hour $^{52}$Cr release assay was used to measure cytotoxicity of LAK cells for tumor cells. Tumor cells at a concentration of about $2 \times 10^6$ and $10 \times 10^6$ were incubated with 50 μCi of $Na_2^{51}CrO_4$ in 0.4 mL of Tris-phosphate buffered saline for 1 hour at 37° C. The cells are washed 4 times with RPMI 1640 containing 5% or 10% fetal calf serum (FCS) and resuspended to $10^5$ cells/mL in cRPMI-20% FCS or RPMI 10% FCS. The effector cells (LAK cells) are suspended to various concentrations and 0.1 mL is added to wells in round bottom microliter plates. The $^{51}$Cr labelled target cells (0.1 mL) are added to all wells and the plates are centrifuged at 200 xg for 5 minutes. After 4 hours of incubation at 37° C., the plates are centrifuged again and 0.1 mL of resulting supernatant is removed from each well and counted in a gamma counter. Percent cytotoxicity is calculated from the following formula:

$$\% \text{ cytotoxicity} = \frac{\text{experimental cpm} - \text{spontaneous cpm}}{\text{total cpm} - \text{spontaneous cpm}} \times 100$$

Each variable is tested in triplicate and the resulting data is expressed as % cytotoxicity or lytic units as indicated. One lytic unit equals the number of tumor cells $\times 10^2$ lysed by $8 \times 10^3$ effector cells. The lytic units are calculated from a plot of the % cytotoxicity vs effector cell/target cell ratio from all ratios tested using a power curve formula. Thus, the reported lytic units reflect the activity measured at all effector to target cell ratios. In some example total yield of lytic units based on the initial population of PBMC is calculated. This cytotoxicity test is further described in "Selected Methods in Cellular Immunology", Mishell and Shiigi, eds., 124–137, W. H. Freeman and Co., San Francisco (1980).

EXAMPLE 1

PBMC were obtained by Ficoll-Hypaque separation of EDTA-anticoagulated venus blood drawn from two healthy consenting human donors. The cells which contained 25% monocytes were washed three times with SBSS and resuspended in RPMI 1640 medium supplemented with 1 mM L-glutamine, 1% penicillin-streptomycin, 1% antibiotic-antimycotic solution, 20 mM HEPES and 10% HIS. The PBMC were separated and suspended to $5 \times 10^6$ cells/mL in serumless RMPI 1640. The suspended PBMC were incubated with various concentrations of L-phenylalanine methyl ester or L-leucine methyl ester(control) as indicated in Table 1 for 40 minutes in 50 mL polypropylene conical tubes at ambient temperature. The resulting lymphocyte cells which contained less than 2% monocytes were washed twice with cold SBSS and resuspended in cRPMI—10% HIS.

These lymphocytes were cultured with 1500 pM purified natural IL-2 at $5 \times 10^6$ cells/mL for 4 days at 37° C. in the presence of 4% $CO_2$. After the culture period, the resulting LAK cells were harvested and resuspended in cRPMI supplemented with 20% fetal calf serum (FCS) (Sterile Systems, Logan, UT) for cytotoxicity assay using Raji cells (Burketts lymphoma) as target cells. The results are presented in Table 1 wherein data in the column labelled "lytic units" represent the mean of duplicate runs and wherein data in the other column are based on mononuclear cells initially placed in culture. The "untreated cells" were mononuclear cells cultured at $1 \times 10^6$ cells/mL in the presence of 1500 pM IL-2.

TABLE 1

|  | Lytic Units | Lytic Units/ $10^6$ mononuclear cells |
|---|---|---|
| untreated cells | 46 | 353 |
| 5 mM Leu-OMe | 12 | 74 |
| 2.5 mM Leu-OMe | 14 | 92 |
| 1 mM Leu-OMe | 39 | 280 |
| 5 mM Phe-OMe | 62 | 404 |
| 2.5 mM Phe-OMe | 56 | 388 |
| 1 mM Phe-OMe | 57 | 465 |

EXAMPLE 2

PBMC were obtained by Ficoll-Hypaque separation of EDTA-anticoagulated venus blood drawn from healthy consenting donors. The cells were washed three times with PBS and resuspended in RPMI 1640 medium supplemented with 1 mM L-glutamine, 1% penicillin-streptomycin, 1% antibiotic-antimycotic solution, 20 mM HEPES and 10% fetal calf serum (FCS). the PBMC were separated and resuspended to $1 \times 10^7$ cells/mL in RPMI 1640 containing 10% FCS. The resuspended PBMC were incubated with various concentrations of L-phenylalanine methyl ester, L-phenylalanine ethyl ester (Phe-OEt), L-phenylalanine t-butyl ester (Phe-Ot-Bu), L-glutamic dimethyl ester (Glu-(OMe)$_2$), L-tyrosine methyl ester (Tyr-OMe) or L-leucine methyl ester (control for 40 minutes in 50 mL polypropylene conical tubes at ambient temperature. The resulting peripheral blood lymphocytes were washed twice with cold RPMI and resuspended in RPMI—10% FCS.

Unless otherwise stated, these lymphocytes were cultured with medium or 10 units/mL rIL-2 at $5 \times 10^6$ to $1 \times 10^7$ cells/mL for 4 days at 37° C. in the presence of 5% of $CO_2$. After the culture period, the resulting LAK cells were harvested and resuspended in RPMI supplemented with 10% FCS for cytotoxicity asay using Raji cells, K562 cells or fresh tumor cells as target cells. The results are presented in Tables 2 and 3 wherein activity is expressed as % cytotoxicity ±SEM of triplicate determinations. The effector to target cell ratio was 20 to 1. Target cells (TC) used are coded as follows Raji cells (R), K562 (K) and fresh tumor cells (F). One unit of IL-2 is defined as that quantity of IL-2 needed to stimulate 50% uptake of radiolabeled (tritium) thymidine by murine tumor-specific cytotoxic T cell lines (CTLL) standardized against Jurkat IL-2 as set forth more fully in Gehmans, et al., *Journal of Immunological Methods* 74, 39–47 (1984), which is incorporated herein by reference.

TABLE 2

| Ester | Conc.(mM) | TC | % Cytotoxicity Medium | rIL-2 |
|---|---|---|---|---|
|  | 0 | K | 6.8 ± 0.5 | 20.5 ± 0.5 |
| Tyr-OMe | 1 | K | 31.8 ± 0.9 | 72.4 ± 1.0 |
|  | 2.5 | K | 71.4 ± 0.9 | 82.0 ± 5.9 |
|  | 5 | K | 55.0 ± 1.3 | 75.4 ± 2.1 |
| Phe-OMe | 1 | K | 32.9 ± 0.9 | 67.4 ± 0.4 |
|  | 2.5 | K | 53.6 ± 0.6 | 78.9 ± 0.8 |
|  | 5 | K | 75.7 ± 3.3 | 79.7 ± 1.7 |
| Leu-OMe | 2.5 | K | 1.6 ± 0.6 | 1.3 ± 0.1 |
|  | 5 | K | 1.6 ± 0.4 | 1.1 ± 0.8 |
|  | 0 | K | 3.6 ± 0.5 | 23.8 ± 0.9 |
| Glu-(OMe)$_2$ | 1 | K | 12.0 ± 1.4 | 52.0 ± 1.4 |
|  | 2.5 | K | 55.1 ± 1.3 | 72.0 ± 3.0 |
|  | 5 | K | 47.8 ± 2.1 | 68.8 ±-1.7 |
| Phe-OMe | 5 | K | 46.6 ± 0.6 | 68.4 ± 0.9 |
|  | 0 | R | 0.9 ± 0.2 | 7.8 ± 0.3 |
| Glu-(OMe)$_2$ | 1 | R | −0.1 ± 0.4 | 31.9 ± 1.4 |
|  | 2.5 | R | 22.0 ± 0.6 | 66.9 ± 1.9 |
|  | 5 | R | 19.4 ± 1.0 | 59.6 ± 3.3 |
| Phe-OMe | 5 | R | 18.5 ± 1.0 | 73.0 ± 2.0 |
|  | 0 | R | −0.2 ± 0.5 | 2.6 ± 0.5 |
| Tyr-OMe | 1 | R | 1.0 ± 0.1 | 46.1 ± 1.0 |
|  | 2.5 | R | 15.4 ± 0.8 | 43.3 ± 3.3 |
|  | 5 | R | 12.6 ± 1.0 | 46.8 ± 4.9 |
| Phe-OMe | 1 | R | 0 | 29.7 ± 2.9 |
|  | 2.5 | R | 6.9 ± 0.3 | 64.3 ± 3.7 |
|  | 5 | R | 11.7 ± 0.7 | 64.9 ± 2.8 |
| Leu-OMe | 2.5 | R | −1.0 ± 0.4 | 0.4 ± 0.9 |
|  | 5 | R | 0 ± 1.0 | 0.3 ± 0.8 |
|  | 0 | F | 1.7 ± 1.0 | 2.2 ± 1.7 |
| Tyr-OMe | 1 | F | 4.5 ± 0.7 | 39.6 ± 1.0 |
|  | 2.5 | F | 16.6 ± 0.2 | 47.0 ± 0.7 |
|  | 5 | F | 13.9 ± 0.4 | 46.9 ± 3.1 |
| Phe-OMe | 1 | F | 3.0 ± 0.8 | 19.2 ± 3.4 |
|  | 2.5 | F | 8.5 ± 1.4 | 41.0 ± 1.7 |
|  | 5 | F | 19.0 ± 1.0 | 50.6 ± 2.5 |
| Leu-OMe | 2.5 | F | 2.3 ± 1.0 | 1.0 ± 0.7 |
|  | 5 | F | 2.1 ± 0.2 | 0.3 ± 1.7 |

TABLE 3

| Ester | TC | Medium | % Cytotoxicity rIL-2(1 u/mL) | rIL-2(10 u/mL) |
|---|---|---|---|---|
| none | K | 2.4 ± 1.0 | 15.1 ± 0.8 | 16.5 ± 0.4 |
| Phe-OMe (5mM) | K | 20.6 ± 0.3 | 32.5 ± 0.4 | 38.4 ± 0.4 |
| Phe-OEt (2.5 mM) | K | 11.0 ± 0.1 | 27.8 ± 0.2 | 32.8 ± 1.5 |
| Phe-OEt (5 mM) | K | 15.3 ± 0.7 | 36.9 ± 1.4 | 42.2 ± 1.3 |
| Phe-Ot-Bu (2.5 mM) | K | 1.9 ± 0.9 | 12.8 ± 0.7 | 18.0 ± 1.6 |
| Phe-Ot-Bu (5 mM) | K | >.0 ± 0.3 | 14.9 ± 0.6 | 26.5 ± 1.8 |
| none | R | 1.0 ± 0.5 | 5.8 ± 0.5 | 9.3 ± 0.7 |
| Phe-OMe (5 mM) | R | 9.0 ± 0.4 | 18.5 ± 0.8 | 29.4 ± 0.5 |
| Phe-OEt (2.5 mM) | R | 3.6 ± 0.3 | 17.5 ± 3.2 | 21.6 ± 0.7 |
| Phe-OEt (5 mM) | R | 5.4 ± 0.7 | 22.3 ± 1.3 | 25.1 ± 1.3 |
| Phe-Ot-Bu (2.5 mM) | R | 1.9 ± 0.2 | 5.3 ± 0.4 | 17.1 ± 0.9 |
| Phe-Ot-Bu (5 mM) | R | 4.9 ± 0.7 | 6.8 ± 0.4 | 15.1 ± 0.6 |

EXAMPLE 3

Using experimental procedures similar to those of Example 2, PBMC were treated with the L-amino acid methyl esters stated in Table 4, cultured and then subjected to a cytotoxicity assay. The results are presented in Table 4 where the abbreviations are as follows: Trp—tryptophan; Asp—aspartic acid; Cys—crysteine; Val—valine; and Ala—alanine.

TABLE 4

| Ester | Conc.(mM) | TC | % Cytotoxicity Medium | rIL-2 (10 u/mL) |
|---|---|---|---|---|
|  | 0 | R | 1.4 ± 0.8 | 15.6 ± 1.0 |
| Trp-OMe | 2.5 | R | 8.9 ± 0.7 | 34.1 ± 1.3 |
|  | 5 | R | 8.6 ± 1.4 | 31.9 ± 1.1 |
| Asp-OMe | 0 | R | 4.5 ± 0.3 | 15.6 ± 2.2 |
|  | 2.5 | R | 7.3 ± 1.0 | 34.9 ± 0.7 |
|  | 5 | R | 16.9 ± 0.7 | 55.2 ± 1.1 |
| Cys-OMe | 0 | R | 1.7 ± 0.1 | 15.6 ± 0.5 |
|  | 1 | R | 7.0 ± 0.9 | 28.5 ± 0.7 |
|  | 2.5 | R | 10.0 ± 0.5 | 47.1 ± 0.8 |
|  | 5 | R | 10.6 ± 0.5 | 36.3 ± 0.7 |
| proline-OMe | 2.5 | R | 1.9 ± 0.1 | 16.4 ± 0.4 |
|  | 5 | R | 5.4 ± 0.2 | 25.7 ± 0.4 |
| Val-OMe | 0 | R | 6.7 ± 0.3 | 28.7 ± 0.4 |
|  | 2.5 | R | 26.4 ± 0.9 | 46.4 ± 2.2 |
|  | 5 | R | 23.0 ± 0.5 | 47.2 ± 0.1 |
| Ala-OMe | 2.5 | R | 11.1 ± 0.6 | 25.7 ± 0.4 |
|  | 5 | R | 23.1 ± 0.2 | 46.7 ± 0.9 |
| Glu-OMe | 0 | R | 4.9 ± 0.2 | 13.3 ± 0.2 |
|  | 2.5 | R | 6.4 ± 0.5 | 32.0 ± 1.7 |
|  | 5 | R | 13.7 ± 0.1 | 37.6 ± 1.2 |

The invention being claimed is:

1. In a process for preparing lymphokine activated killer cells wherein peripheral blood mononuclear cells are cultured to produce a population of cells which are cytotoxic for natural killer cell resistant tumor cells, the improvement comprising contacting said peripheral blood mononuclear cells or peripheral blood lymphocytes resulting therefrom with an L-amino acid lower alkyl ester or hydrogen chloride salt thereof, wherein the L-amino acid is selected from the group consisting of alanine, aspartic acid, cysteine, glutamic acid, glutamine, phenylalanine, proline, tyrosine, tryptophan and valine or a mixture of any of the foregoing, and thereafter culturing the resulting cells.

2. A process according to claim 1 wherein said peripheral blood mononuclear cells are human cells.

3. In a process for preparing lymphokine activated killer cells wherein human peripheral blood mononuclear cells are cultured to produce a population of cells which are cytotoxic for natural killer cell resistant tumor cells, the improvement comprising contacting said human peripheral blood mononuclear cells or peripheral blood lymphocytes resulting therefrom with an L-amino acid lower alkyl ester or hydrogen chloride salt thereof, wherein the L-amino acid is selected from group consisting of alanine, aspartic acid, cysteine, glutamic acid, glutamine, phenylalanine, proline, tyrosine, tryptophan and valine or a mixture of any of the foregoing, and thereafter culturing the resulting cells.

4. A process according to claim 3 wherein the contacting is performed for a period of at least about 15 minutes.

5. A process according to claim 4 wherein the period is from about 20 minutes to about 40 minutes.

6. A process according to claim 5 wherein the hydrogen chloride salt of amino acid lower alkyl ester is used in a concentration of from about 1 to 5 mM.

7. A process according to claim 6 wherein the amino acid is phenylalanine or tyrosine.

8. A process according to claim 7 wherein the lower alkyl group is methyl, ethyl or t-butyl.

9. A process according to claim 8 wherein the lower alkyl group is methyl.

10. A process according to claim 9 wherein the amino acid is phenylalanine.

11. A process according to claim 4 wherein the human peripheral blood mononuclear cells or peripheral blood lymphocytes resulting therefrom are cultured in the presence of interleukin-2.

12. A process according to claim 6 wherein the human peripheral blood mononuclear cells or peripheral blood lymphocytes resulting therefrom are cultured in the presence of interleukin-2.

13. A process according to claim 4 wherein the human peripheral blood mononuclear cells or peripheral blood lymphocytes are cultured in the absence of interleukin-2.

14. A process according to claim 6 wherein the human peripheral blood mononuclear cells or peripheral blood lymphocytes are cultured in the absence of interleukin-2.

15. A process according to claim 12 wherein the peripheral blood lymphocytes are contacted with the hydrogen chloride salt of the amino acid lower alkyl ester.

16. A process according to claim 12 wherein the human peripheral blood mononuclear cells are contacted with the hydrogen chloride salt of the amino acid lower alkyl ester.

17. A process according to claim 16 wherein the peripheral blood lymphocytes obtained by contacting with the amino acid lower alkyl ester are washed and resuspended.

18. A process according to claim 17 wherein the resuspended peripheral blood lymphocytes are cultured for 2–7 days in the presence of recombinant interleukin-2 at a concentration of from about 150 pM to 15,000 pM.

19. A process according to claim 18 wherein the recombinant interleukin-2 concentration is from about 1000 pM to about 2000 pM.

20. A process according to claim 19 wherein the concentration of peripheral blood lymphocytes is from about $1 \times 10^6$ cells/mL to about $1 \times 10^8$ cells/mL.

21. A process according to claim 20 wherein the amino acid is phenylalanine or tyrosine.

22. A process according to claim 21 wherein the lower alkyl group is methyl or ethyl.

23. A process according to claim 22 wherein the amino acid is phenylalanine.

24. A process according to claim 23 wherein the lower alkyl group is methyl.

25. A composition consisting essentially of isolated, lymphokine activated killer cells prepared according to the process of claim 6, said cells being in a pharmaceutically acceptable carrier and being reactive to tumor when administered with interleukin-2 to a human afflicted with said tumor.

26. A composition consisting essentially of isolated, lymphokine activated killer cells prepared according to the process of claim 10, said cells being in a pharmaceutically acceptable carrier and being reactive to tumor when administered with interleukin-2 to a human afflicted with said tumor.

27. A composition consisting essentially of isolated, lymphokine activated killer cells prepared according to the process of claim 19, said cells being in a pharmaceutically acceptable carrier and being reactive to tumor when administered with interleukin-2 to a human afflicted with said tumor.

28. A composition consisting essentially of isolated, lymphokine activated killer cells prepared according to the process of claim 21, said cells being in a pharmaceutically acceptable carrier and being reactive to tumor when administered with interleukin-2 to a human afflicted with said tumor.

29. A composition consisting essentially of isolated, lymphokine activated killer cells prepared according to the process of claim 23, said cells being in a pharmaceutically acceptable carrier and being reactive to tumor when administerd with interleukin-2 to human afflicted with said tumor.

30. A method of treating a tumor comprising contacting the tumor with interleukin-2 and a tumor size-reducing effective amount of a composition according to claim 26.

31. A method of treating a tumor comprising contacting the tumor with interleukin-2 and a tumor size-reducing effective amount of a composition according to claim 27.

32. A method of treating a tumor comprising contacting the tumor with interleukin-2 and a tumor size-reducing effective amount of a composition according to claim 28.

33. A method of treating a tumor comprising contacting the tumor with interleukin-2 and a tumor-size reducing effective amount of a composition according to claim 29.

34. A method of treating cancer in humans comprising administering to a human suffering from said cancer interleukin-2 and a tumor size-reducing effective amount of a composition according to claim 26.

35. A method of treating cancer in humans comprising administering to a human suffering from said cancer interleukin-2 and a tumor size-reducing effective amount of a composition according to claim 27.

36. A method of treating cancer in humans comprising administering to a human suffering from said cancer interleukin-2 and a tumor size-reducing effective amount of a composition according to claim 28.

37. A method of treating cancer in humans comprising administering to a human suffereing from said cancer interleukin-2 and a tumor size-reducing effective amount of a composition according to claim 29.

* * * * *